(12) United States Patent
MacMillan et al.

(10) Patent No.: US 7,597,686 B2
(45) Date of Patent: Oct. 6, 2009

(54) VALVES AND SUCTION CATHETER ASSEMBLIES

(75) Inventors: Nicholas Paul MacMillan, Dover (GB); Ian Douglas Stace, Minster-in-Thanet (GB); Neil Steven Veasey, Ashford (GB)

(73) Assignee: Smiths Group PLC, London (GB)

( * ) Notice: Subject to any disclaimer, the term of this patent is extended or adjusted under 35 U.S.C. 154(b) by 839 days.

(21) Appl. No.: 10/765,953

(22) Filed: Jan. 29, 2004

(65) Prior Publication Data

US 2004/0182393 A1    Sep. 23, 2004

(30) Foreign Application Priority Data

Feb. 27, 2003   (GB) ................. 0304457.5
Oct. 8, 2003    (GB) ................. 0323511.6

(51) Int. Cl.
*A61M 5/00*   (2006.01)
(52) U.S. Cl. ...................... 604/249; 251/318
(58) Field of Classification Search ................. 251/318; 604/33, 35, 119, 246, 249
See application file for complete search history.

(56) References Cited

U.S. PATENT DOCUMENTS

| | | | |
|---|---|---|---|
| 3,146,987 A | 9/1964 | Krayl | |
| 3,456,679 A | 7/1969 | Grahan | |
| 3,828,982 A | * 8/1974 | Steigerwald | ........... 222/153.11 |
| 4,121,619 A | 10/1978 | Pauliukonis | |
| 4,430,073 A | 2/1984 | Bemis et al. | |
| 4,569,344 A | 2/1986 | Palmer | |
| 4,638,539 A | 1/1987 | Palmer | |
| 4,836,199 A | 6/1989 | Palmer | |
| 4,846,216 A | 7/1989 | Raymond | |
| 4,872,579 A | 10/1989 | Palmer | |
| 5,215,522 A | 6/1993 | Page et al. | |
| 5,269,768 A | 12/1993 | Cheung | |
| 5,277,177 A | 1/1994 | Page et al. | |
| 5,297,776 A | 3/1994 | Dieringer | |
| 5,300,043 A | 4/1994 | Devlin et al. | |
| 5,320,328 A | * 6/1994 | Decloux et al. | ............. 251/326 |
| 5,592,727 A | 1/1997 | Glowa et al. | |
| 5,919,174 A | * 7/1999 | Hanson | ....................... 604/533 |
| 2002/0063230 A1 | 5/2002 | Cavagna | |

FOREIGN PATENT DOCUMENTS

| | | |
|---|---|---|
| DE | 24 55 260 | 5/1976 |
| DE | 20315718 | 11/2004 |
| GB | 2 274 901 | 8/1994 |
| WO | 99/58186 | 11/1999 |
| WO | WO 99/58186 | 11/1999 |

* cited by examiner

*Primary Examiner*—Kevin C Sirmons
*Assistant Examiner*—Deanna K Hall
(74) *Attorney, Agent, or Firm*—Louis Woo

(57) ABSTRACT

A suction control valve for a closed system suction catheter has a housing with an inlet bore and an outlet bore inclined at an angle to the inlet bore and opening into the bore via an aperture. A valve member comprises a rod member and a manually actuable plate extending longitudinally in an external channel along the housing between two walls. The rod member supports a resilient sleeve and its forward end is urged, by a spring, to engage a tapered seal within the housing forwardly of the aperture, thereby blocking flow through the valve. The valve is opened by sliding the plate rearwardly so that the valve member moves rearwardly of the aperture. A locking cap can be twisted to prevent movement of the valve member from its closed position.

13 Claims, 2 Drawing Sheets

VALVES AND SUCTION CATHETER ASSEMBLIES

BACKGROUND OF THE INVENTION

This invention relates to valves and suction catheter assemblies.

Closed system suction catheter assemblies are used to remove secretions from within a tracheal tube or the respiratory passages of a patient. The assembly comprises a manifold at one end with a sliding seal through which a suction catheter can be advanced and withdrawn. A flexible envelope is joined at one end to the manifold and encloses the catheter along its length. The other end of the envelope and the catheter are joined with a rear end component including a suction control valve and a connector. The connector connects the catheter to a suction source and the valve enables the clinician to control the suction applied by the catheter.

Suction catheter assemblies are disposable, single-patient items so it is important that their cost is low. The cost of the valve contributes a significant part to the overall cost of the assembly so it is important that this can be made at low cost whilst also operating efficiently with low risk of blockage and leakage. Various forms of suction control valves have been described previously such as in U.S. Pat. No. 5,269,768, U.S. Pat. No. 5,300,043, U.S. Pat. No. 4,569,344, U.S. Pat. No. 4,638,539, U.S. Pat. No. 4,836,199, U.S. Pat. No. 4,872,579, U.S. Pat. No. 5,277,177 and U.S. Pat. No. 5,215,522. There are also applications other than closed system suction catheters where similar forms of valves are required.

BRIEF SUMMARY OF THE INVENTION

It is an object of the present invention to provide an alternative valve and a suction catheter assembly including such a valve.

According to one aspect of the present invention there is provided a valve for controlling flow of fluid along a passage defined by a first bore and a second bore opening into the first bore through an aperture, the valve including a valve member slidable in alignment with the first bore, the valve member having sealing means and being movable from a first position where the sealing means is on a side of the aperture remote from the first bore such as to allow fluid flow between the first and second bores to a second position on an opposite side of the aperture to block flow of fluid between the first and second bores.

The valve preferably includes resilient means arranged to urge the valve member to the second position. The resilient means may be a helical spring. The valve member may be arranged to engage a tapered sealing formation in the second position. The valve member preferably includes a rod-shape member and the sealing means preferably includes a cylindrical sleeve of a resilient material supported on the rod-shape member. The cylindrical sleeve may have an outwardly-projecting annular flange arranged to make a wiping seal with a bore. The second bore is preferably inclined at an angle relative to the first bore, such as substantially 45°. The valve member preferably includes a plate member arranged for manual engagement, the plate member being slidably located in a channel along an outer surface of a housing of the valve. The housing may include two walls, the channel extending between the two walls so that the plate member is protected by the walls. The walls preferably have an upper surface that is curved such that the height of the walls varies along the length of the valve. The valve preferably includes a locking member operable to prevent movement of the valve member. The locking member is preferably rotatable such as a rotatable cap located at one end of the valve. The locking member may include a projection movable into and out of alignment with the valve member so as to prevent or enable movement of the valve member. The locking member may include two projections that form a continuation of two walls on a housing of the valve when the locking member is in a position to enable movement of the valve member. The locking member may be arranged to displace the valve member by a short distance towards a sealing formation when the locking member is moved to its locking position, such as to enhance the seal with the sealing formation. The valve may include a housing of a transparent material.

According to another aspect of the present invention there is provided a suction catheter assembly including a suction catheter and a valve according to the above one aspect of the invention connected at a machine end of the catheter.

According to a third aspect of the present invention there is provided a suction catheter assembly of the kind including a suction catheter, a suction control valve towards the rear end of the assembly by which suction applied to the catheter can be controlled, a patient end manifold by which the assembly is connected with a tracheal tube, and a flexible envelope extending between the manifold and the control valve around the catheter, the suction control valve having a user-actuable member for controlling opening and closing of the valve and the user-actuable member being movable substantially axially of the catheter from a forward, closed position to a rear, open position.

A closed system suction catheter assembly including a suction control valve, according to the present invention, will now be described, by way of example, with reference to the accompanying drawings.

DETAILED DESCRIPTION OF THE PREFERRED EMBODIMENT

Figure 1:
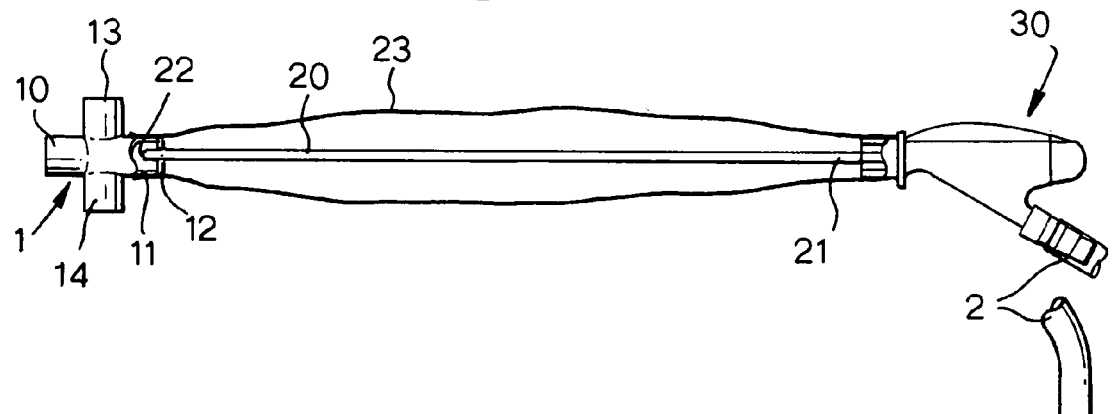
FIG. 1 is a side elevation view of the assembly.

With reference first to FIG. 1, the assembly includes a forward or patient end manifold coupling 1 having a first port 10 adapted to connect to a standard 15 mm tracheal connector of the kind fitted to the machine end of a tracheal tube. At the opposite end of the coupling 1, and aligned with the first port 10, is a second port 11 containing a wiping seal 12 through which the suction catheter 20 can be extended and withdrawn. The coupling 1 has two further ports 13 and 14 aligned with one another and extending at right angles to the first and second ports 10 and 11. These further ports 13 and 14 are connected to two limbs of a patient ventilation system (not shown). The ports may have swivels. Alternative forms of coupling are possible, such as with only one further port.

The suction catheter 20 is flexible, typically being about 500 mm long and having an external diameter of about 5 mm. The rear, machine end 21 of the catheter 20 is connected to a suction control valve 30 and its forward end 22 locates just forwardly of the seal 12 in the patient end coupling 1. A flexible envelope 23 extends around the catheter 20, its forward end being joined to the coupling 1 and its rear end being joined to the housing of the suction control valve 30. The flexible nature of the envelope 23 enables the catheter 20 to be pushed forwardly or pulled rearwardly through the seal 12 by manipulation through the envelope. The length of the envelope 23 is chosen to prevent the forward end 22 of the catheter 20 being pulled through the seal 12. The suction control valve 30 connects via tubing 2 to a suction source 3. As so far described, the assembly is conventional.

Figure 2:
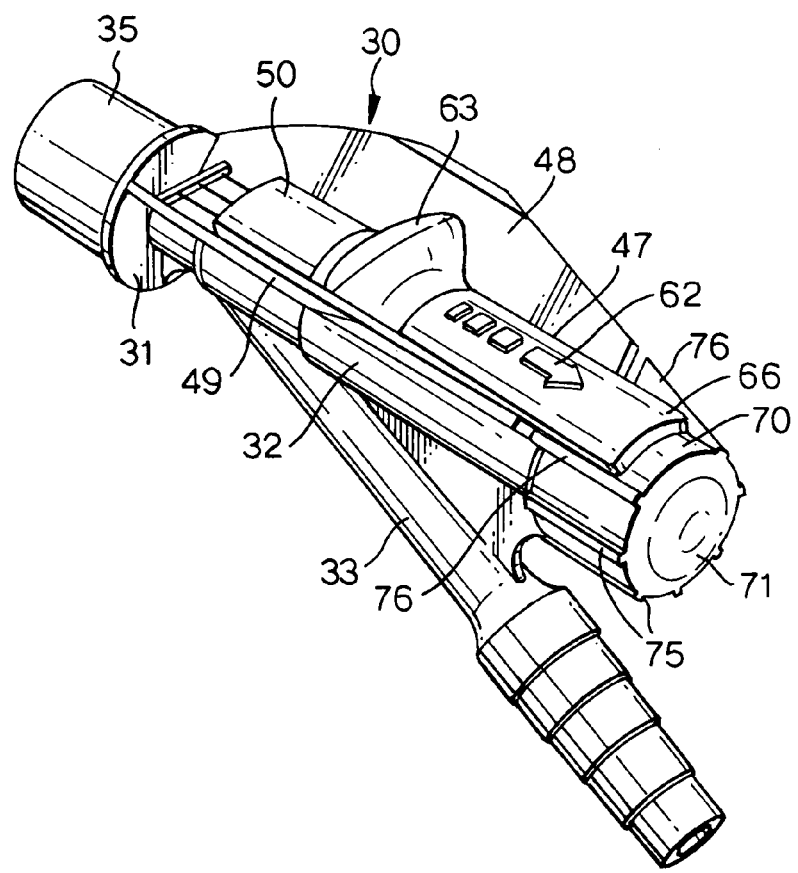
FIG. 2 is a perspective view of the valve from the rear end, to one side and above when unlocked.
Figure 3:
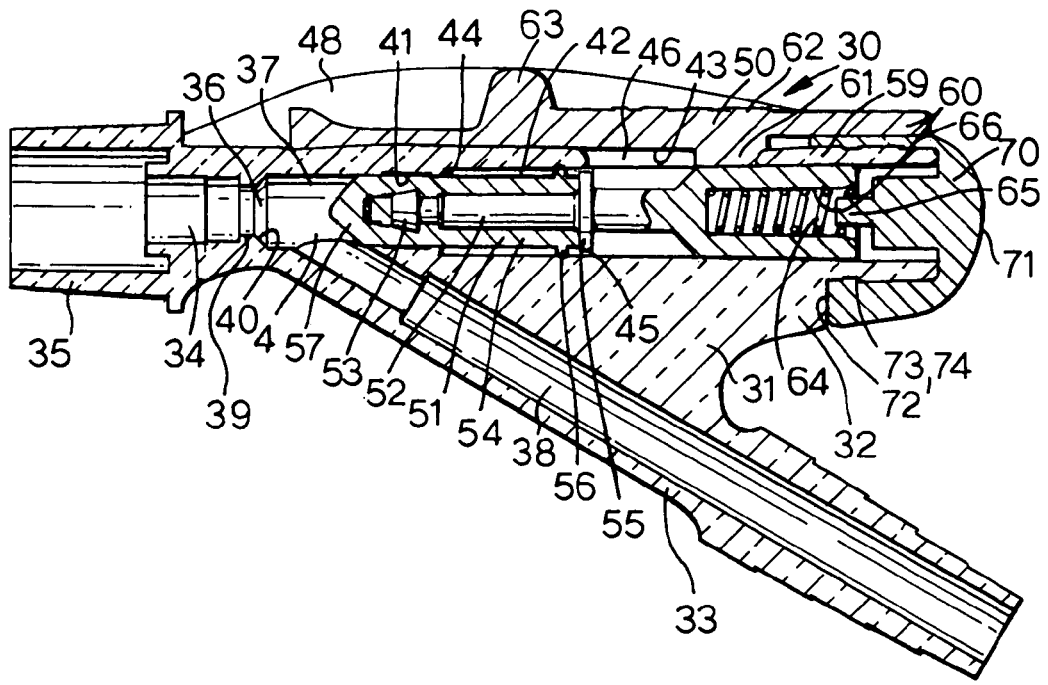
FIG. 3 is a sectional elevation view of the valve in an open state.
Figure 4:
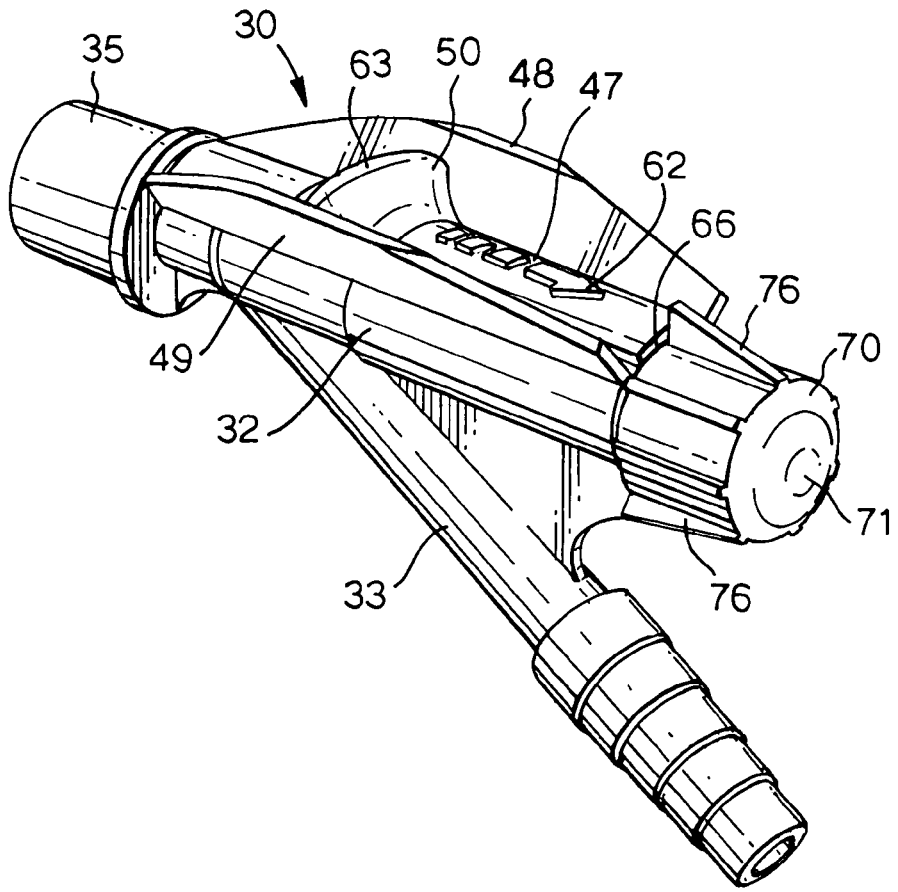
FIG. 4 is a perspective view of the valve when closed and locked.

With reference now also to FIGS. 2 to 4, the suction control valve 30 differs from previous valves in that it is operated by a slider 50. This can be locked in a closed position by a rotatable cap 70 at the end of the valve.

The valve 30 has an outer housing 31 of a rigid, transparent plastics material, such as polycarbonate, having a main body portion 32 extending axially of the catheter 20 and an outlet connection arm 33 inclined downwardly at an angle of about 30°. The angle of the outlet connection arm 33 is chosen to enable the valve 30 to be held comfortably in the hand, with the fingers under the arm and the thumb on top of the main body portion 32. The lower, free end of the arm 33 is tapered and stepped so that the suction tubing 2 can be pushed onto the arm and retained securely in position.

The rear end 21 of the suction catheter 20 is bonded into a short, tapered bore 34 located concentrically within an outer collar 35 at the forward end of the body portion 32. The rear end of the envelope 23 is secured between the outside of the collar 35 and an outer ring (not shown) fitted over the collar. The bore 34 communicates with a fluid passageway 36 through the valve 30 provided by a first passage or bore 37 extending axially within the main body portion 32 and a second passage or bore 38 extending through the outlet connection arm 33 and opening into the first bore through an aperture 4. The bore 37 has an internal annular step 39 located just forwardly of the aperture 4. The step 39 has a tapering, sealing surface formation 40 on its rear-facing side.

The rear part of the bore 37 beyond the step 39 is divided into three sections 41, 42 and 43 separated from one another by two shallow internal steps 44 and 45 (FIG. 3). The rear section 43, beyond the step 45, opens via a slot 46 into a channel 47 extending forwardly axially along the upper surface of the main body portion 32. The channel 47 extends between two side walls 48 and 49, which extend longitudinally of the housing 31 and have a curved upper edge highest midway along their length. The walls 48 and 49 project outwardly at an angle of about 45° to the vertical so that they are oriented at about 90° to one another.

The housing 31 contains a user-actuable valve member in the form of the slider 50, which is moulded of a hard, coloured plastics material, and which may be coded for different sizes. The valve member 50 has an internal, sealing portion 51 provided by a rod-shape piston 52 with an enlarged end 53 and supporting a cylindrical sleeve 54 of a soft, resilient elastomeric material. The rear end of the sleeve 54 abuts a flange 55 on the piston 52 and itself has an outwardly-projecting annular sealing flange 56 with a rounded edge. The diameter of the flange 56 is chosen so that it makes a sliding, wiping seal with the intermediate section 42 of the rear part of the bore 37. The sleeve 54 has a constant diameter forwardly of the flange 55. The forward end 57 of the sleeve 54 is closed and has a conical shape providing a sealing surface. Alternatively, the seal could be provided by one or more sealing rings mounted on the piston.

The piston 52 has an enlarged, barrel-shape rear end portion 59 with a cylindrical recess 60 extending axially and opening at its rear. A short beam 61 projects upwardly from the rear portion 59 through the slot 46 to the underside of an integral, cantilevered slider plate 62. The slider plate 62 is wider than the piston 52 and has a laterally-extending thumb bar 63 projecting from its upper surface about two-thirds the way along its length towards the forward end of the slider. The slider plate 62 extends forwardly parallel with the piston along the channel 47 in the upper surface of the housing 31 so that the thumb bar 63 is accessible to the user. The top of the thumb bar 63 lies slightly below the upper edge of the walls 48 and 49 so that it is protected by the walls.

The housing 31 also contains a resilient member in the form of a helical, stainless steel spring 64, although other springs of a non-ferrous material, such as a hard plastics material, for example, polycarbonate, could be used. The spring 64 aligns axially of the bore 37 and is located between the rear, right-hand end of the valve member 50 and the inside of the housing 31. More particularly, the forward, left-hand end of the spring 64 locates in the recess 60 in the valve member 50 and its rear, right-hand end extends around a peg 65, which projects axially from the rear end cap 70.

The cap 70 has a generally cylindrical shape with a closed, rounded rear end 71 and an open forward end 72. The cap 70 is retained on the rear end of the housing 31 by an interengaging projection 73 and recess 74 on the outside of the housing and on the inside of the cap. The projection 73 and recess 74 are shaped to allow the cap 70 to be rotated about the axis of the bore 37 through an angle of about 40°. On its external surface the cap 70 has several longitudinally-extending shallow ribs 75 to improve grip when twisting the cap (FIG. 2). The cap 70 also has two larger fins 76 of triangular shape that form a continuation of the walls 48 and 49 when the cap is rotated into alignment, in an unlocked position. The external surface of the cap 70 between the two fins 76 is shaped to enable the rear end 66 of the slider plate 62 to move rearwardly between the fins when the cap is in the unlocked position with the fins aligned with the walls 48 and 49, as shown in FIG. 2. If, however, the cap 70 is rotated through 40°, as shown in FIG. 4, one of the fins 76 will be moved to lie between the walls 48 and 49 in the path of the slider plate 62 and will prevent the plate being moved rearwardly. This effectively locks the valve 30 in its closed position. The cap 70 remains in its locked position by friction, a detent or the like until the user needs to unlock the valve.

The natural position of the valve 30 is where the spring 64 urges the valve member 50 forwardly to its full extent. In this position, the forward, conical end 57 of the sealing sleeve 54 is held against the tapered surface 40 on the step 39 to form a fluid seal. Because this seal is located between the bores 37 and 38, forwardly of the aperture 4, there can be no flow of material through the valve 30. The seal formed by the flange 56 at the rear end of the sleeve 54 with the intermediate section 42 of the rear part of the bore 37 provides an additional, dynamic, wiping seal to prevent escape of material from the valve; it also prevents passage of air to the suction bore 38 from the interior of the housing 31. When the cap 70 is turned to a locked position, one of the fins 76 is a slight interference fit across the rear end 66 of the slider 62, thereby pushing it slightly forwards and improving the seal between the forward end 57 of the sleeve 54 and the sealing surface 40.

To open the valve 30 and allow suctioning, the user ensures the valve is in an unlocked state, grips the thumb bar 63 with his thumb and slides the slider 50 rearwardly to its full extent against the action of the spring 64 to the position shown in FIG. 3. In this position, the forward end 57 of the sealing portion 51 is held to the rear of the aperture 4 so that material can flow from the main bore 37 to the suction bore 38. Suction applied by the suction source 3 to the suction bore 38 is communicated to the main bore 37 via the aperture 4 and, therefore, to the bore of the suction catheter 20 so that secretions or the like can be removed when the tip 22 of the catheter is advanced into the tracheal tube.

When released, the spring 64 returns the valve member 50 to its natural, forward, closed or sealing position.

When the valve 30 is open there is no impediment to flow between the two bores 37 and 38, compared with some previous valves where there is a risk that the valve member might cause solid materials carried in the fluid to block the valve. The open flow path makes it easier to clean, thereby enabling the assembly to be used for longer periods with low risk of infection. Even when the valve is unlocked, the sliding action needed to open it minimizes the risk of inadvertent actuation compared with some previous valves actuated by a pressdown action. The two side walls effectively protect the slider from inadvertent contact. The axial sliding motion needed to operate the valve encourages the user to pull back the catheter in a straighter fashion when withdrawing from the tracheal tube. This reduces the risk that the catheter will be kinked. The locking arrangement enables the user to lock the valve closed when desired. Its construction also makes it readily apparent how the lock can be released when this is needed. The construction of the valve enables it to be gas sterilized in its natural, closed state because gas can penetrate all parts of the valve through its bores and the slot 46. The transparent housing enables the user to confirm the absence of blockages within the valve. Its simple construction enables the valve to be produced at low cost and with a low weight, thereby minimizing forces applied to the tracheal tube. The valve can be used with single lumen catheters, as described, or with double lumen catheters where the additional lumen is for supply of an irrigating fluid.

The valve is not limited to use with suction catheters but could be used in other applications for controlling flow of fluid.

What we claim is:

1. A suction catheter assembly comprising a suction catheter and a valve for controlling flow along said suction catheter, said valve comprising: a housing defining a first bore in communication with said suction catheter and a second bore extending to an outlet opening into said first bore through an aperture; a valve member, said valve member having a sealing surface and being slidable in alignment with said first bore from a first position where said sealing surface is on a side of said aperture remote from said first bore such as to allow unobstructed fluid flow from said suction catheter along the first bore to the second bore to a second position on an opposite side of said aperture to block flow of fluid from said suction catheter between said first and second bores, wherein said valve includes a rotatable locking member operable to prevent movement of said valve member, wherein said locking member is mounted on said housing and has an external surface formation that is out of alignment with a part of said valve member when said locking member is rotatable between a first position where said valve member is free for sliding movement, to a second position where said external surface formation is in alignment with said part of said valve member so as to hinder movement of said valve member.

2. A suction valve assembly according to claim 1 including a spring, wherein said spring is arranged to urge said valve member to said second position.

3. A suction valve assembly according to claim 2, wherein said spring is helical.

4. A suction valve assembly according to claim 1, wherein said housing defines a tapered sealing formation, and wherein said valve member is arranged to engage said sealing formation in said second position.

5. A suction valve assembly according to claim 1, wherein said cylindrical sleeve has an outwardly-projecting annular flange arranged to make a wiping seal with a bore in said housing.

6. A suction valve assembly according to claim 1, wherein said second bore is inclined at an angle relative to said first bore.

7. A suction valve assembly according to claim 6, wherein said angle is substantially 45°.

8. A suction valve assembly according to claim 1, wherein said housing has a channel extending along an outer surface, and wherein said valve member includes a plate member arranged for manual engagement and slidably located in said channel.

9. A suction valve assembly according to claim 8, wherein said housing includes two walls, and wherein said channel extends between said two walls so that said plate member is protected by said walls.

10. A suction valve assembly according to claim 9, wherein said walls have an upper surface that is curved such that the height of said walls varies along the length of the valve.

11. A suction valve assembly according to claim 1, wherein said housing has two walls extending longitudinally, and wherein said locking member includes two projections that form a continuation of said two walls when said locking member is in a position to enable movement of said valve member.

12. A suction valve assembly according to claim 1, wherein said housing has a sealing formation, and wherein said locking member is arranged to displace said valve member by a short distance towards said sealing formation when said locking member is moved to its locking position, such as to enhance the seal with said sealing formation.

13. A suction valve assembly according to claim 1, wherein said housing is of a transparent material.

* * * * *